(12) United States Patent
Koven

(10) Patent No.: US 10,383,380 B2
(45) Date of Patent: Aug. 20, 2019

(54) YOGA APPARATUS

(71) Applicant: myAVA, LLC, New Haven, CT (US)

(72) Inventor: Laura Koven, Paris, TN (US)

(73) Assignee: myAVA, LLC, New Haven, CT (US)

( * ) Notice: Subject to any disclaimer, the term of this patent is extended or adjusted under 35 U.S.C. 154(b) by 112 days.

(21) Appl. No.: 15/802,825

(22) Filed: Nov. 3, 2017

(65) Prior Publication Data

US 2018/0110269 A1 Apr. 26, 2018

Related U.S. Application Data

(63) Continuation of application No. 15/215,245, filed on Jul. 20, 2016, now abandoned.

(Continued)

(51) Int. Cl.
*A41F 1/06* (2006.01)
*A43B 5/00* (2006.01)
(Continued)

(52) U.S. Cl.
CPC ......... *A41D 19/0041* (2013.01); *A41D 13/06* (2013.01); *A41D 13/081* (2013.01); *A41D 27/08* (2013.01); *A41F 1/06* (2013.01); *A41F 19/00* (2013.01); *A61B 5/11* (2013.01); *A63B 71/1225* (2013.01); *A63B 71/14* (2013.01); *A63B 71/141* (2013.01); *G06F 19/3481* (2013.01); *G06K 9/00342* (2013.01); *G09B 19/0038* (2013.01); *G16H 20/30* (2018.01); *A41B 11/001* (2013.01); *A41D 2300/50* (2013.01); *A41D 2400/80* (2013.01); *A41D 2400/82* (2013.01); *A43B 5/00* (2013.01); *A63B 21/4015* (2015.10);

(Continued)

(58) Field of Classification Search
CPC ........ A63B 71/14–141; A41D 19/0051; A41D 13/08–084; G09B 19/003–0038
See application file for complete search history.

(56) References Cited

U.S. PATENT DOCUMENTS 645,406 A 3/1900 Potter
2,700,159 A 1/1955 Denburgh
(Continued)

FOREIGN PATENT DOCUMENTS

WO WO 2012/058725 5/2012

OTHER PUBLICATIONS

U.S. Appl. No. 15/215,245 (U.S. Pat. Pub. No. 2017/0020212).
(Continued)

*Primary Examiner* — Jennifer M Deichl
(74) *Attorney, Agent, or Firm* — Frost Brown Todd LLC

(57) ABSTRACT

An athletic strap includes a glove portion including a plantar aspect, a dorsal aspect, and a cavity defined between the plantar and dorsal aspects. The cavity is configured to receive at least part of a hand or a foot of a user. The glove portion further includes a first opening at one end of the glove portion and a second opening at another end of the glove portion. The first and second openings provide ingress to or egress from the cavity. The glove portion further includes a strip extending between the plantar and dorsal aspects. The strip is adjacent to the second opening. The glove portion further includes a first indicium disposed on the plantar aspect. The first indicium extends along a first axis. The first axis is coincident with a portion of the strip.

20 Claims, 11 Drawing Sheets

Related U.S. Application Data

(60) Provisional application No. 62/254,548, filed on Nov. 12, 2015, provisional application No. 62/194,663, filed on Jul. 20, 2015.

(51) Int. Cl.

| | | |
|---|---|---|
| *A61B 5/11* | (2006.01) | |
| *G06K 9/00* | (2006.01) | |
| *A41B 11/00* | (2006.01) | |
| *A41D 13/06* | (2006.01) | |
| *A41D 13/08* | (2006.01) | |
| *A41D 19/00* | (2006.01) | |
| *A41D 27/08* | (2006.01) | |
| *A41F 19/00* | (2006.01) | |
| *A63B 21/00* | (2006.01) | |
| *A63B 23/00* | (2006.01) | |
| *A63B 71/06* | (2006.01) | |
| *A63B 71/12* | (2006.01) | |
| *A63B 71/14* | (2006.01) | |
| *G06F 19/00* | (2018.01) | |
| *G09B 19/00* | (2006.01) | |
| *G16H 20/30* | (2018.01) | |

(52) U.S. Cl.
CPC ..... *A63B 21/4019* (2015.10); *A63B 2023/006* (2013.01); *A63B 2071/0694* (2013.01); *A63B 2071/1283* (2013.01)

(56) References Cited

U.S. PATENT DOCUMENTS

| | | | |
|---|---|---|---|
| 3,501,773 A | 3/1970 | Stansberry et al. | |
| 3,581,312 A | 6/1971 | Nickels | |
| 4,561,122 A | 12/1985 | Stanley et al. | |
| 4,958,384 A | 9/1990 | McCrane | |
| 5,033,119 A | 7/1991 | Wiggins | |
| 5,295,269 A | 3/1994 | Ballard | |
| 5,500,956 A | 3/1996 | Schulkin et al. | |
| 5,517,694 A | 5/1996 | Fabry | |
| 5,528,772 A | 6/1996 | Cheek | |
| 5,557,806 A | 9/1996 | Caswell et al. | |
| 5,581,809 A | 12/1996 | Mah | |
| 5,774,895 A | 7/1998 | Baldwin | |
| 6,199,211 B1 | 3/2001 | Franzolino | |
| 6,408,442 B1 | 6/2002 | Kang | |
| 6,810,531 B1 | 11/2004 | Lento | |
| 6,895,598 B1 | 5/2005 | Sokolowski | |
| 7,383,591 B1* | 6/2008 | Getzwiller | A41B 11/08 2/161.1 |
| 7,856,739 B2 | 12/2010 | Terlizzi et al. | |
| D635,737 S | 4/2011 | Ash et al. | |
| 9,066,546 B2 | 6/2015 | Getzwiller et al. | |
| 2004/0060096 A1 | 4/2004 | Thiruppathi | |
| 2009/0144880 A1 | 6/2009 | Desjardin et al. | |
| 2010/0031411 A1 | 2/2010 | Andrews | |
| 2010/0313332 A1 | 12/2010 | Denis | |
| 2011/0099676 A1* | 5/2011 | Getzwiller | A41D 13/06 2/16 |
| 2011/0113530 A1 | 5/2011 | Ballard et al. | |
| 2012/0023633 A1 | 2/2012 | Kummerfeldt | |
| 2012/0090073 A1 | 4/2012 | Chen | |
| 2012/0100941 A1 | 4/2012 | Finelli | |
| 2013/0236866 A1* | 9/2013 | MaLossi | G09B 19/00 434/247 |
| 2014/0215686 A1 | 8/2014 | McMakin, Jr. | |
| 2015/0080193 A1 | 3/2015 | Redmond et al. | |
| 2017/0020212 A1 | 1/2017 | Koven | |

OTHER PUBLICATIONS

International Search Report and Written Opinion dated Oct. 13, 2016 for International PCT Application No. PCT/US2016/043157.
U.S. Appl. No. 62/194,663, filed Jul. 20, 2015.
U.S. Appl. No. 62/254,548, filed Nov. 12, 2015.

* cited by examiner

YOGA APPARATUS

PRIORITY

This application claims priority to U.S. application Ser. No. 15/215,245, entitled "YOGA APPARATUS", filed Jul. 20, 2016, which claims priority to both Provisional Application No. 62/194,663, entitled "YOGA APPARATUS", filed Jul. 20, 2015 and Provisional Application No. 62/254,548, entitled "YOGA APPARATUS," filed Nov. 12, 2015, the disclosures of which are hereby incorporated by reference, in their entireties.

TECHNICAL FIELD

Embodiments of the technology relate, in general, to athletic apparel technology, and in particular to safety apparel for yoga and athletic applications.

BACKGROUND

The use of a flexible mat that can be rolled out for use during a yoga or other exercise class and then rolled back up once the class is complete is common. These mats are intended to protect the user from slipping on the floor or from otherwise touching or laying on the floor, which can be uncomfortable and unsanitary. Yoga mats are often referred to as "sticky mats" because they also have a textured surface that can help prevent slipping. During certain types of yoga, such as Bikram yoga, temperatures can exceed 105 degrees Fahrenheit. During this and other types of "hot" yoga a towel is often placed on top of the mat by practitioners to absorb sweat and to decrease the chances of slippage.

BRIEF DESCRIPTION OF THE DRAWINGS

The present disclosure will be more readily understood from a detailed description of some example embodiments taken in conjunction with the following figures.

DETAILED DESCRIPTION

Figure 1A:
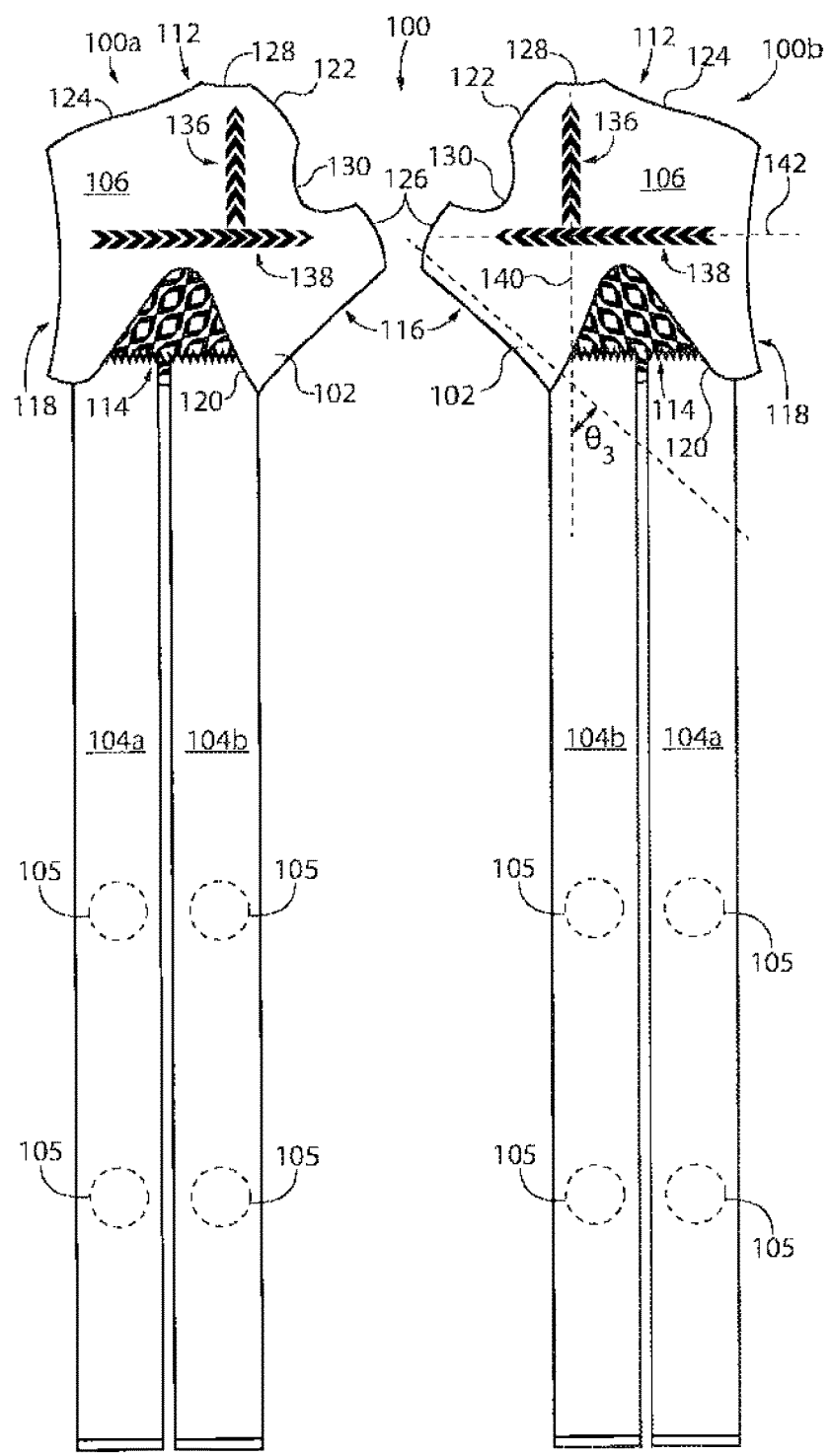
FIG. 1A depicts a top elevational view of a pair of athletic hand straps that are suitable for use in yoga applications.
Figure 1B:
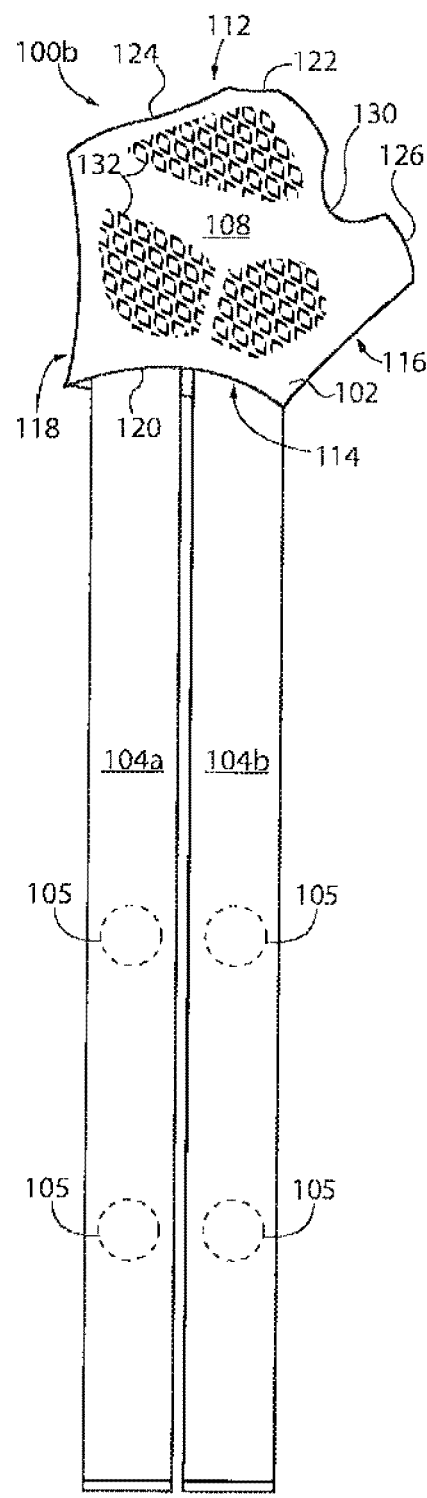
FIG. 1B depicts a bottom elevational view of one of the athletic hand straps shown in FIG. 1A.
Figures 2A, 2B:
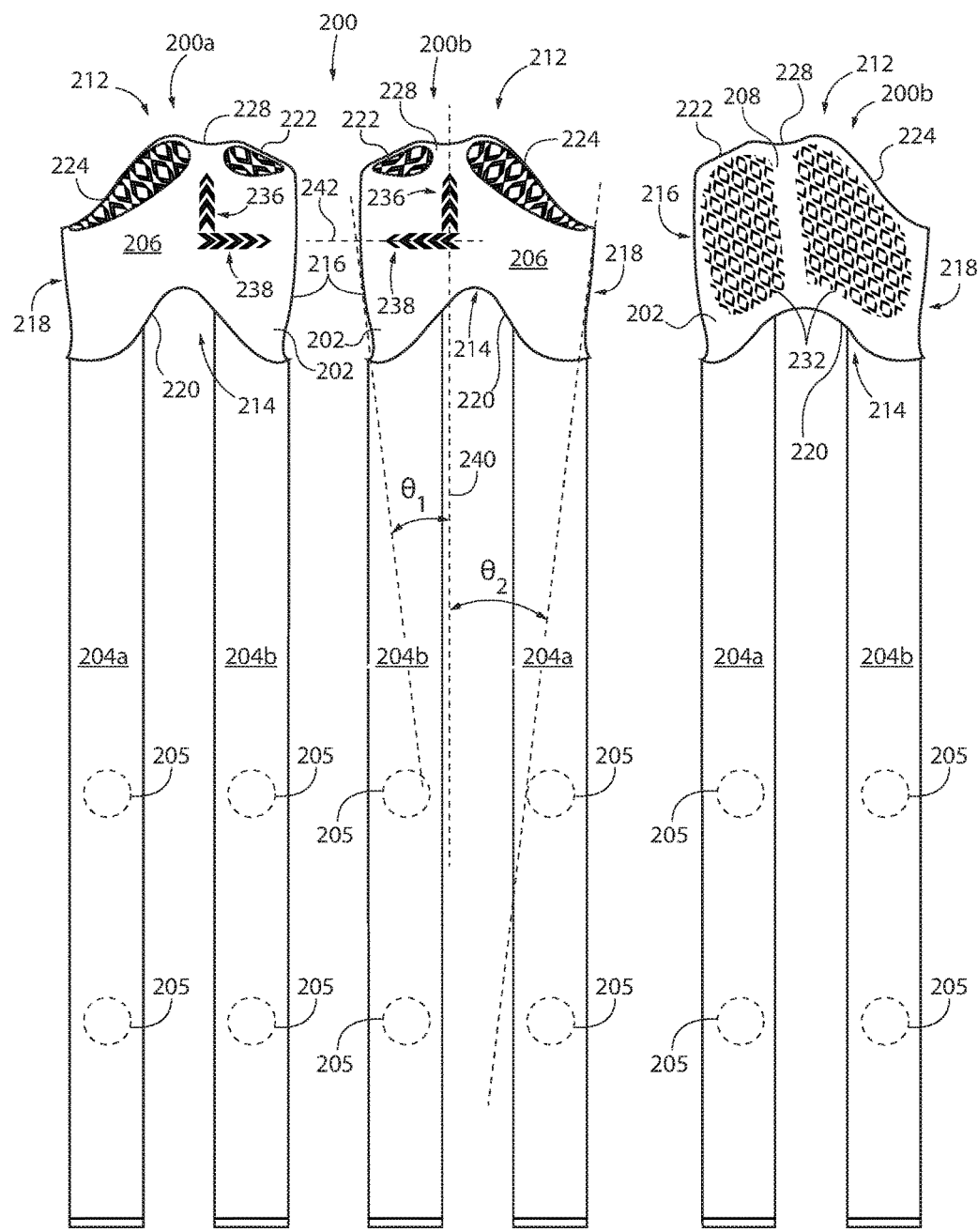
FIG. 2A depicts a top elevational view of a pair of athletic foot straps that are suitable for use in yoga applications.
FIG. 2B depicts a bottom elevational view of one of the athletic foot straps shown in FIG. 2A.
Figure 3:
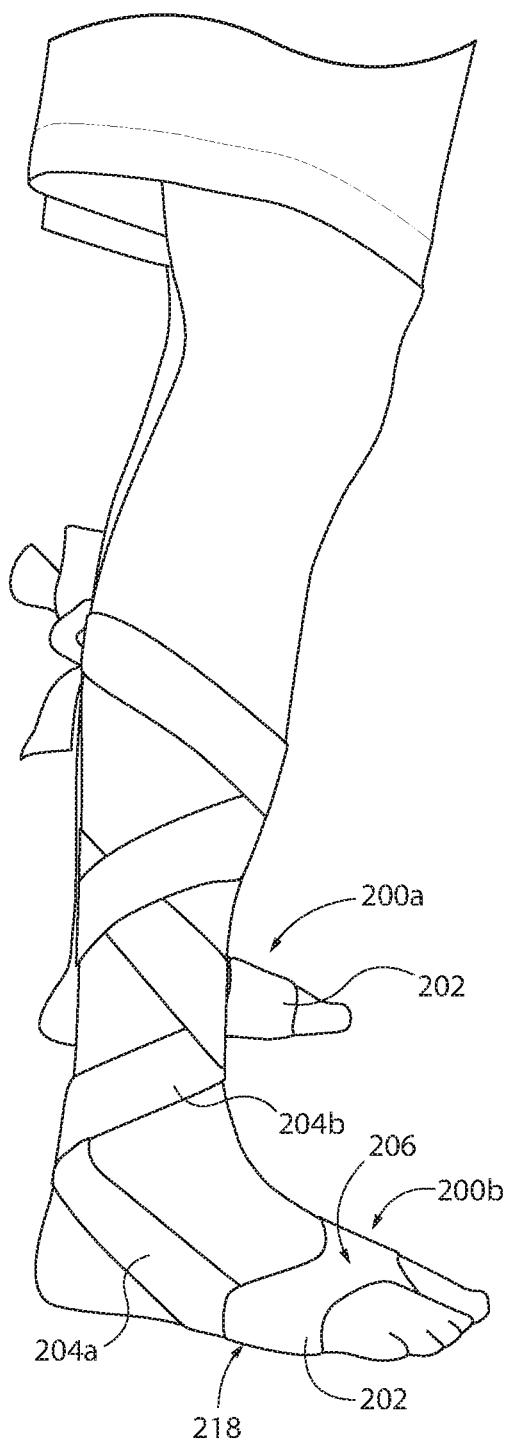
FIG. 3 shows a side elevational view of one of the athletic foot straps of FIG. 2A being worn on the foot and the leg of a user.

Various non-limiting embodiments of the present disclosure will now be described to provide an overall understanding of the principles of the structure, function, and use of the proficiency tracking systems and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment or example is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

It will be appreciated that anatomical reference terms "proximal," "distal," "medial," "lateral," "dorsal," "plantar," "ventral," "top," "bottom," "side," and other spatial reference terms are used for convenience and clarity to with respect to positions and placement of athletic equipment. However, athletic equipment such as that described herein is used in many orientations and positions, and these terms are not intended to be limiting and absolute.

Example embodiments described herein can improve safety, balance, technique, and performance for an athlete, such as a yoga practitioner. For example, yoga is often done in extremely warm or even hot environments with an ambient temperature in excess of 100 degrees Fahrenheit. In such environments a user or practitioner may sweat profusely, which can lead to potentially dangerous slippage, alignment issues, and accidents that can result in injury. Towels that may be used in such situations may have a limited coverage area, may bunch, may slip, may become saturated, or may otherwise not mitigate or even cause a potentially dangerous condition. Embodiments described herein can include providing a wearable piece of athletic equipment that can reduce slippage, help promote proper alignment, and help with flexibility. The athletic straps described herein can increase the coefficient of friction between the user's hands and the mat. In at least one embodiment, the user may be able to perform yoga techniques without a mat by using only the athletic straps. During hot yoga, the user may not need the use of a towel to achieve a sufficient grip on the floor or mat.

As discussed in further detail a plurality of athletic straps are shown that can be worn on the hands or feet of practitioners. The athletic straps can be configured for any suitable activity, such as yoga or hot yoga, and can help prevent practitioners from slipping during such activities. It will be appreciated that the athletic straps are shown by way of example only and any suitable configuration, material, shape, and use is contemplated.

FIGS. 1A, 1B, 4 and 5 show details of one embodiment of pair of athletic hand straps (100) that are configured to be placed or worn on the hand of a user. The athletic straps (100) can have any suitable modification for use on the hand such as a gloved shape that substantially matches the contour of a hand. While the present disclosure discusses straps (100) being worn on both hands, it is contemplated that a user may only wear only one strap (100) on one hand.

As shown, left strap (100a) is configured to be placed or worn on the left hand, while right strap (100b) is configured to be placed or worn on the right hand. It will be understood that one or both straps may be utilized or worn during an exercise routine, such as a yoga routine, in some examples. Particularly, hand straps (100a, 100b) may be worn on the hands of a user while foot straps (200) (discussed below) may be worn on the feet of a user during a yoga routine, for example. Each of the athletic straps (100a, 100b) includes a sheath or glove portion (102) and a pair of athletic bands (104a, 104b) extending from the glove portion (102). Bands (104a, 104b) may be tied or otherwise secured around the wrist and forearm of a user. As shown, sheath (102) includes a dorsal aspect (106) and a plantar aspect (108) that define a cavity (110) into which a user may slip his or her hand for a substantially snug fit between the hand and the sheath (102). Sheath (102) includes a distal portion (112), a proximal portion (114), a medial portion (116), and a lateral portion (118). Sheath (102) includes a proximal opening (120) at the proximal portion (114), and a set of distal first and second openings (122, 124) at the distal portion (112), and a medial opening (126). A first strip (128) of material extends from the plantar portion (108) to the dorsal portion (106) and between distal first and second openings (122, 124) at the distal portion (112). A second strip (130) of material extends from the plantar portion (108) to the dorsal portion (106), and between the first opening (120) and the medial opening (126). As shown, second strip (130) comprises a seam. The distal first opening (122) is configured to accommodate the index or fore finger while the distal second opening (124) is configured to accommodate the remaining fingers when the user inserts his or her hand into the sheath (102). The medial opening (126) is configured to accommodate the thumb when the user inserts his or her hand into the sheath (102). Other suitable configurations of strips and openings to accommodate and secure the fingers, thumb and hand within sheath (102) will be apparent to persons skilled in the art in view of the teachings herein.

In some examples, sheath (102) may include more or less than the number of strips shown. For example, sheath (102) may include multiple strips, such as an amount of strips sufficient to define openings for each of the five fingers, or for less than each of the five fingers. The strips, alone or in combination with a retention force from other portions of the sheath (102), can retain the user's hand relative to the sheath (102). For example, strips may prevent the user's hand from passing through the sheath (102) during use. In other examples, sheath (102) may not include any strips. In such examples, the sheath (102) may be configured and sized to retain a user's hand relative to sheath (102) during use, absent the strip(s). In some examples, the sheath (102) may include other features within cavity (110) that help retain the hand relative to sheath (102). For example, as shown in FIG. 1A, sheath includes internal treading or a surface effect within cavity (110) that can reduce slippage of the hand within or relative to cavity. Suitable other manners of retaining a user's hand relative to sheath will be understood by persons skilled in the art in view of the teachings herein.

Hand straps (100a, 100b) of the present example each include a first band (104a) and a second band (104b) that can be affixed at a first end to the sheath (102). The bands (104a, 104b) can be affixed in any suitable manner and can be permanently affixed or selectively detachable. The bands (104a, 104b) can be secured to sheath (102) at about the opening (120) of the cavity (110) and can extend away from the sheath (102), or in the proximal direction. Bands (104a, 104b) can have any suitable length such as between about 6 inches and about 36 inches in some examples, or between about 12 inches and about 24 inches in other examples. Bands (104a, 104b) can be made out of any suitable material, such as elastic materials, and can have any suitable dimensions. It will be appreciated that embodiments are contemplated that include only a sheath (102), but do not include associated bands (104a, 104b). It will be appreciated that any suitable number of bands (104a, 104b) are contemplated, including only a single band or three or more bands. In the examples shown in FIGS. 1A-1B, bands (104a, 104b) include securing features or fasteners that allow the bands (104a, 104b) to be secured to the arm or wrist of a user. As shown, securing features or fasteners (105) comprise a male snap and a female snap. In other examples, however, one of the bands may include a male snap while the other of the bands (104a, 104b) includes a female snap. Other suitable configurations of snaps will be apparent to persons skilled in the art in view of the teachings herein.

Figure 4:
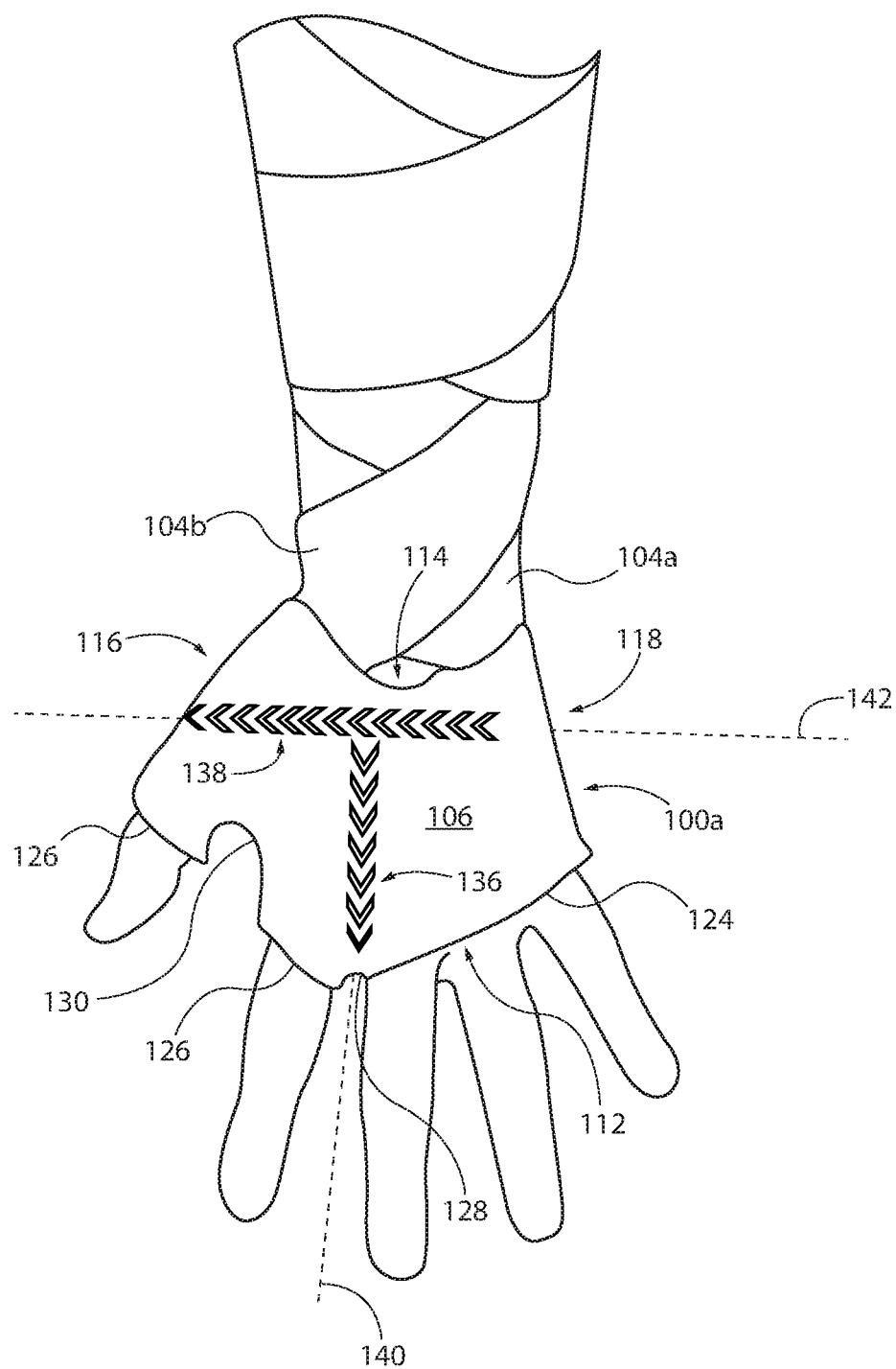
FIG. 4 depicts a top view of one of the athletic hand straps of FIG. 1A being worn on the hand and arm of a user.
Figure 5:
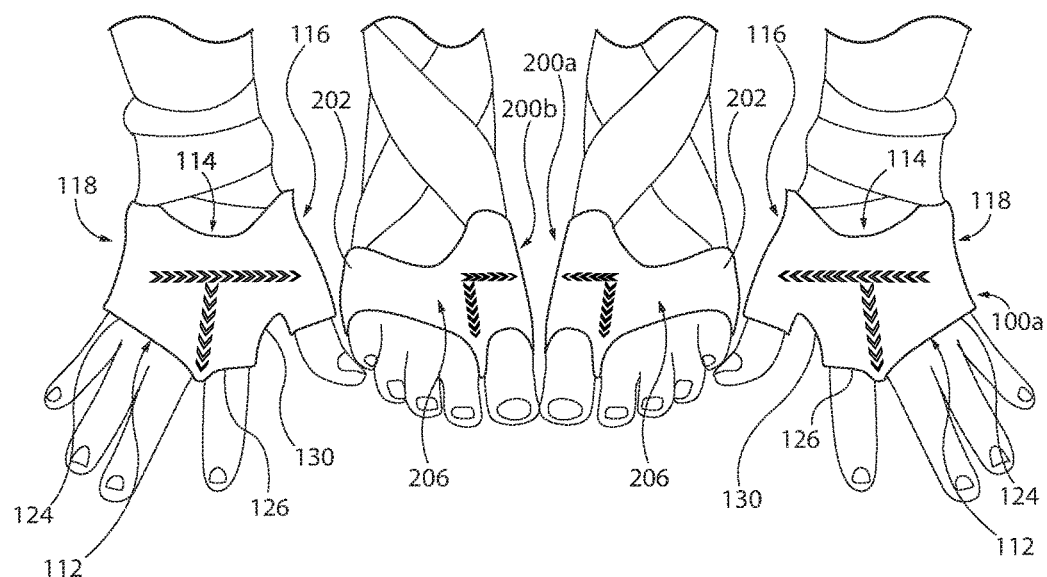
FIG. 5 depicts a perspective view of the athletic straps of FIG. 1A being worn on the hands and arms of a user and the athletic foot straps of FIG. 2A being worn on the feet and legs of the user, showing alignment features of the athletic straps of FIGS. 1A and 2A to assist the user with placement of the hands and feet during a yoga exercise.

During use the athletic straps (100a, 100b) can be worn by a user such that the user's hand is placed within the sheath (102) and the bands (104a, 104b) are tied or wrapped around the wrist and forearm of the user (see FIGS. 4-5). It will be appreciated that any style of wrapping configuration of bands (104a, 104b) and utilization of fastener (134) (or lack thereof) is contemplated. For example, as illustrated, the bands (104a, 104b) can be tied together by the user once a secure fit is provided. As discussed above, the bands (104a, 104b) can also include other fasteners (105), such as mechanical fasteners, hook and loop fasteners, a clasp, a drawstring, or the like to facilitate closure. It may be beneficial to permit a quick release such that the bands (104a, 104b) can be used as part of an exercise as described herein. Although bands (104a, 104b) are described, it will be appreciated that a second sheath or modified sock can also be used to cover a portion of the ankle or leg to secure the athletic strap (100a, 100b) to the user.

In some examples, the athletic straps (100, 200) can include a plurality of markings on the dorsal surface of the sheaths that can assist with proper positioning. For example, during activities such as yoga there are general rules about the positioning of the feet, the hands, and the body relative to the feet and hands. Notations on the sheaths of the athletic straps can provide instruction to users on where their hands and feed should be positioned, for example. Instructors can also reference these notations or markings (discussed in further detail below) and communicate to students, for example, instructions regarding their placement (block 344) during a yoga session. For example, such a yoga session may be one that is led by an instructor where the instructor instructs practitioners to assume particular poses or a series of poses (block 342). It will be appreciated that different notations can be provided for different activities or types of yoga. In one embodiment, a user can provide their own notations as a reminder for positioning, such as with a washable marker on the sheath of the athletic strap (100, 200). As described, the athletic straps can be flexible or elastic, sized to a specific user, or can be adjustable such as with a VELCRO® attachment (not shown) (i.e., a type of hook-and-loop fastener).

More particularly, in the present example, as shown best in FIGS. 1A, 1B, 4, and 5, sheath (102) includes a first set of indicia (136) and a second set of indicia (138) on the dorsal portion (106). In other examples, there may be a different number of sets of indicia, such as less than two (e.g., zero, one), or more than two (three, four, etc.). As shown, first set of indicia (136) extends along a first axis (140) while second set of indicia (138) extends along a second axis (142). As shown, the first axis (140) and second axis (142) are positioned substantially perpendicular to one another. However, in other examples, first axis (140) and second axis (142) may be positioned at a different oblique angle relative to one another, such as less than about 90 degrees or more than about 90 degrees. In the present example, first axis (140) and second axis (142) each are positioned relative to particular features of straps (100a, 100b). For example, as shown, first axis (140) extends substantially distally-proximally relative to straps (100a, 100b). Particularly, first axis (140) extends through strip (128) extending between the first and second distal openings (122, 124) such that a portion of first axis (140) is coincident with strip (128). As shown, first axis (140) is noncoincident with the first opening and the second opening, such that the first axis extends between the first distal opening (122) and the second distal opening (124) but does not intersect the first or second distal openings (122, 124). Moreover, as shown, first axis (140) extends between and parallel to each of the bands (104a, 104b), and extends coincidently along one of the bands (104a, 104b).

However, in other examples, bands (104a, 104b) may be configured differently such that the first and second axes (140, 142) are positioned differently relative to bands (104a, 104b). In the present example, second axis (142) extends substantially medially-laterally relative to sheath (102). As shown, second axis (142) intersects the medial and distal portions (116, 112) of sheath (102). As shown, second axis (142) does not intersect the proximal opening or the distal first and second openings (122, 124), but does intersect the medial (thumb) opening (116). Put another way, second axis (142) is spaced proximally from the distal first and second openings (122, 124) along first axis (140) and is spaced distally from the proximal opening (120) along the first axis (140).

The first axis (140) is disposed relative to the medial portion (116) of sheath (102) at particular angles to ensure proper alignment during a yoga practice, for example. As shown in the present example, medial portion (116) of sheath (102) extends along a medial axis (144) (which extends parallel to a line that is tangent to the medial portion of sheath). As shown, first axis (140) is disposed relative to medial axis (144) at an angle $\theta_3$. In the present example, $\theta_3$ is between about 20 degrees and about 60 degrees, but in other examples may be between about 30 degrees and about 55 degrees, and in other examples may be about 48 degrees. It will be understood by persons skilled in the art that using a different point of tangency along medial and lateral portions (116, 118) may result in different values of $\theta_3$.

In some examples, straps (100a, 100b) may be configured such that first and second axes (140, 142) and thus first and second sets of indicia (136, 138) are oriented at a predetermined angle relative to a particular anatomical structure when worn by a user. For example, first and/or second axes may be oriented at a predetermined angle(s) relative to one or more bones of the hand, wrist, or arm (e.g., radius, ulna, metacarpals, proximal phalanges, middle phalanges, distal phalanges or other bones), tendons, ligaments, and other relative anatomical structures. It will be understood that such angles may vary depending on the anatomy of a particular user. It will be further understood that such angles may vary depending on the positioning of the hand, that is, whether the hand/wrist is in undergoing pronation, supination, extension, flexion, ulnar deviation, radial deviation, or other movements/positioning, or anatomically possible combinations thereof, or is in a normal resting state.

FIGS. 2A, 2B, 3, and 5 show a set of athletic foot straps (200) comprising a left foot strap (200a) and a right foot strap (200b). As shown, left foot strap (200a) is configured to be placed or worn on the left foot of a user, while right foot strap (200b) is configured to be placed or worn on the right foot of a user.

It will be understood that one or both straps (200a, 200b) may be utilized or worn during an exercise routine, such as a yoga routine, in some examples. Each athletic strap (200a, 200b) includes a sheath or glove portion (202) and a pair of athletic bands (204a, 204b) extending from the sheath (202). As shown, sheath (202) includes a dorsal aspect (206) and a plantar aspect (208) that define a cavity (210) into which a user may slip his or her foot for a substantially snug fit between the foot and the sheath (202). Sheath (202) includes a distal portion (212), a proximal portion (214), a medial portion (216), and a lateral portion (218). Sheath (202) includes an opening (220) at the proximal portion (214) and a set of distal first and second openings (222, 224) at the distal portion (212). A strip of material (228) extends from the plantar portion (208) to the dorsal portion (206) and between first and second openings (222, 224) at the distal portion (212). The strip (228) is positioned such that when a user slips his or her foot into the cavity (210), the distal first opening (222) may accommodate the big toe of a user and the distal second opening (224) may accommodate the remaining toes of the user. In other words, the strip (228) can have a placement similar to a thong-sandal or flip flop. In other examples, sheath (202) may include more or less than one strip at the distal portion (212). For example, sheath may include multiple strips, such as an amount of strips sufficient to define openings for each of the five toes, or for less than each of the five toes.

The strip (228), alone or in combination with a retention force from other portions of the sheath (202), can retain the user's foot relative to the sheath (202). For example, the strip (228) may prevent the user's foot from passing through the sheath (202) during use. In other examples, sheath (202) may not include a strip at the distal portion (212). In such examples, the sheath (202) may be configured and sized to retain a user's foot relative to sheath (202) during use, absent the strip(s). In some examples, the sheath (202) may include other features within cavity that help retain the foot relative to sheath. For example, as shown best in FIG. 2A, sheath includes internal treading or a surface effect within cavity (210) that can reduce slippage of the foot within or relative to sheath (202), as discussed in further detail below. Suitable other manners of retaining a user's foot relative to sheath (202) will be understood by persons skilled in the art in view of the teachings herein. Various sheath sizes can be made available or, in one embodiment, the sheath can be flexible such that the sheath can fit a variety of foot sizes.

In the example shown, an inner surface of the plantar portion (208) of the sheath includes a surface effect, treading, tackiness, or the like that can prevent slippage when the athletic strap is being worn. It will be appreciated that any suitable surface effect that can increase the coefficient of friction is contemplated. In one embodiment, different surface effects can be provided for different environments. For example, during hot yoga where slippage often occurs, a surface with a higher coefficient of friction may be preferred. The tread or the like on the plantar surface (208) of the athletic strap (200a, 200b) can have any suitable configuration where, for example, the tackiness can be positioned on locations that are most likely to slip during use. In one embodiment, the surface effects (232) can be positioned to accommodate a specific type of yoga being performed.

The sheath (202) can have any suitable shape or configuration. The sheath (202), in one embodiment, can include a minimum amount of fabric that can still safely retain the foot of a user. For example, during hot yoga, additional material may be uncomfortable and saturated during use. Providing a breathable open design may be more comfortable for a user. The sheath (202) can be constructed from any suitable material such as neoprene, airprene, plastics, cotton, elastic materials, or the like, including combinations thereof. Materials can have absorbent properties, anti-slippage properties, and the like. The sheath (202) can be provided with pads, internally or externally, that can improve comfort for a user. Although the balls of a user's feet may be a helpful location to position the sheath (202), it is contemplated that the heel of the foot or other regions can be covered and/or include a surface effect as appropriate.

The foot straps (200a, 200b) of the present example include a first band (204a) and a second band (204b) that can be affixed to one another at a first end to the sheath (202). The bands (204a, 204b) can be affixed in any suitable manner and can be permanently affixed or selectively detachable. The bands (204a, 204b) can be secured to back side of the sheath (202) at about the opening (220) of the cavity (220) and can extend proximally. The bands (204a, 204b) can have any suitable length such as between about 6 inches and about 36 inches in some examples, or between about 12 and about 24 inches in other examples. The straps can be made out of any suitable material, such as elastic materials, and can have any suitable dimensions. It will be appreciated that embodiments are contemplated that include only a sheath, but do not include associated straps. It will be appreciated that any suitable number of bands are contemplated, including only a single band or three or more bands. Moreover, although bands (204a, 204b) are described, it will be appreciated that a second sheath or modified sock can also be used to cover a portion of the ankle or leg to secure the athletic straps (200a, 200b) to the user.

During use, athletic straps (200a, 200b) can be worn by a user such that the user's foot is placed within the sheath (202) and the bands (204a, 204b) are tied or wrapped around the ankle and lower leg of the user. It will be appreciated that any style of wrap (e.g., the configuration in which bands (204a, 204b) are wrapped around the legs and ankles) and fastener is contemplated. For example, as illustrated in FIG. 5, the bands can be tied together by the user once a secure fit is provided. The bands can also include fasteners (205), such as mechanical fasteners, hook and loop fasteners, a clasp, a drawstring, or the like to facilitate closure. In some examples, fasteners (205) may comprise snaps that allow the bands (204a, 204b) to be secured to the leg/ankle of a user. In such an example, each band (204a, 204b) may include a male snap and a female snap. In other examples, however, one of the bands (204a, 204b) may include a male snap while the other of the bands (204a, 204b) includes a female snap. In addition or in the alternative, other fastening devices or mechanisms may be utilized in order to affix bands (204a, 204b) to a user. Other suitable configurations of snaps and fastening mechanisms will be apparent to persons skilled in the art in view of the teachings herein. It may be beneficial to permit a quick release such that the bands (204a, 204b) can be used as part of an exercise as described herein.

In the example shown, for reasons similar to sheath (102), each sheath (202) includes a first set of indicia (236) and a second set of indicia (238) on a dorsal aspect (206) thereof. In other examples, there a different number of sets of indicia, such as less than two (e.g., zero, one), or more than two (three, four, etc.). As shown, first set of indicia (236) extends along a first axis (240) while second set of indicia (238) extends along a second axis (242). As shown, the first axis (240) and second axis (242) are positioned substantially perpendicular to one another. However, in other examples, first axis (240) and second axis (242) may be positioned at a different oblique angle relative to one another, such as less than about 90 degrees or more than about 90 degrees. In the present example, first axis (240) and second axis (242) each are positioned relative to particular features of each athletic foot strap (200a, 200b). For example, as shown, first axis (242) extends substantially distally-proximally relative to strap. Particularly, first axis (240) extends through strip (228) such that a portion of first axis (240) is coincident with strip (228). As shown, first axis (240) is noncoincident with the first opening (222) and the second opening (224), such that the first axis extends between the first opening (222) and the second opening (224) but does not intersect the first or second openings (222, 224). Moreover, as shown, first axis (240) extends between and parallel to each of the bands (204a, 204b), but does not intersect or extend over either of bands (204a, 204b). In other words, first axis (240) is offset from bands (204a, 204b) along second axis (242). However, in other examples, bands (204a, 204b) may be configured differently such that the first and second axes (204a, 204b) are positioned differently relative to bands (204a, 204b). In the present example, second axis (242) extends substantially medially-laterally relative to sheath (202). As shown, second axis (242) intersects the medial and distal portions (216, 212) of straps (200a, 200b). As shown, second axis (242) does not intersect the proximal opening (220) or the distal first and second openings (222, 224). In other words, second axis (240) is spaced proximally from the distal first and second openings (222, 224) along first axis (240) and is spaced distally from the proximal opening (220) along the first axis (240).

In the example shown, the first axis (240) is disposed relative to the medial and lateral portions (216, 218) of sheath (202) at particular angles to ensure proper alignment during a yoga practice, for example. As shown in the present example, medial portion (216) of sheath (202) extends along a medial axis (244) while lateral portion (218) of sheath (202) extends along a lateral axis (246). As shown, medial axis (244) particularly extends tangentially relative to a portion of medial portion (216) while lateral axis (246) extends tangentially relative to a portion of lateral portion (218). As shown, first axis (240) is disposed relative to medial axis (244) at an angle $\theta_1$. In the present example, $\theta_1$ is between about 0 degrees and about 20 degrees, but in other examples may be between about 0 degrees and about 8 degrees, and in other examples may be about 6 degrees. As shown, first axis (240) is disposed relative to lateral axis (246) at an angle $\theta_2$. In some examples, $\theta_2$ is between about 0 degrees and about 30 degrees, but in other examples may be between about 2 degrees and about 8 degrees, and in some examples may be about 5 degrees. It will be understood by persons skilled in the art that using a different point of tangency along medial and lateral portions (216, 218) may result in different values of $\theta_1$ and $\theta_2$.

In the examples shown, indicia (136, 138, 236, 238) each comprise a plurality of chevron symbols. In other examples, however, one or more of indicia (136, 138, 236, 238) may be any other types of indicia such as dots, arrows, lines, and any other suitable shapes, sizes, etc. In some examples, any of indicia (136, 138, 236, 238) may be a single element, such as a line, arrow, or other element, rather than a plurality of elements. Other suitable configurations of indicia (136, 138, 236, 238) will be apparent to persons skilled in the art in view of the teachings herein.

Figure 6:
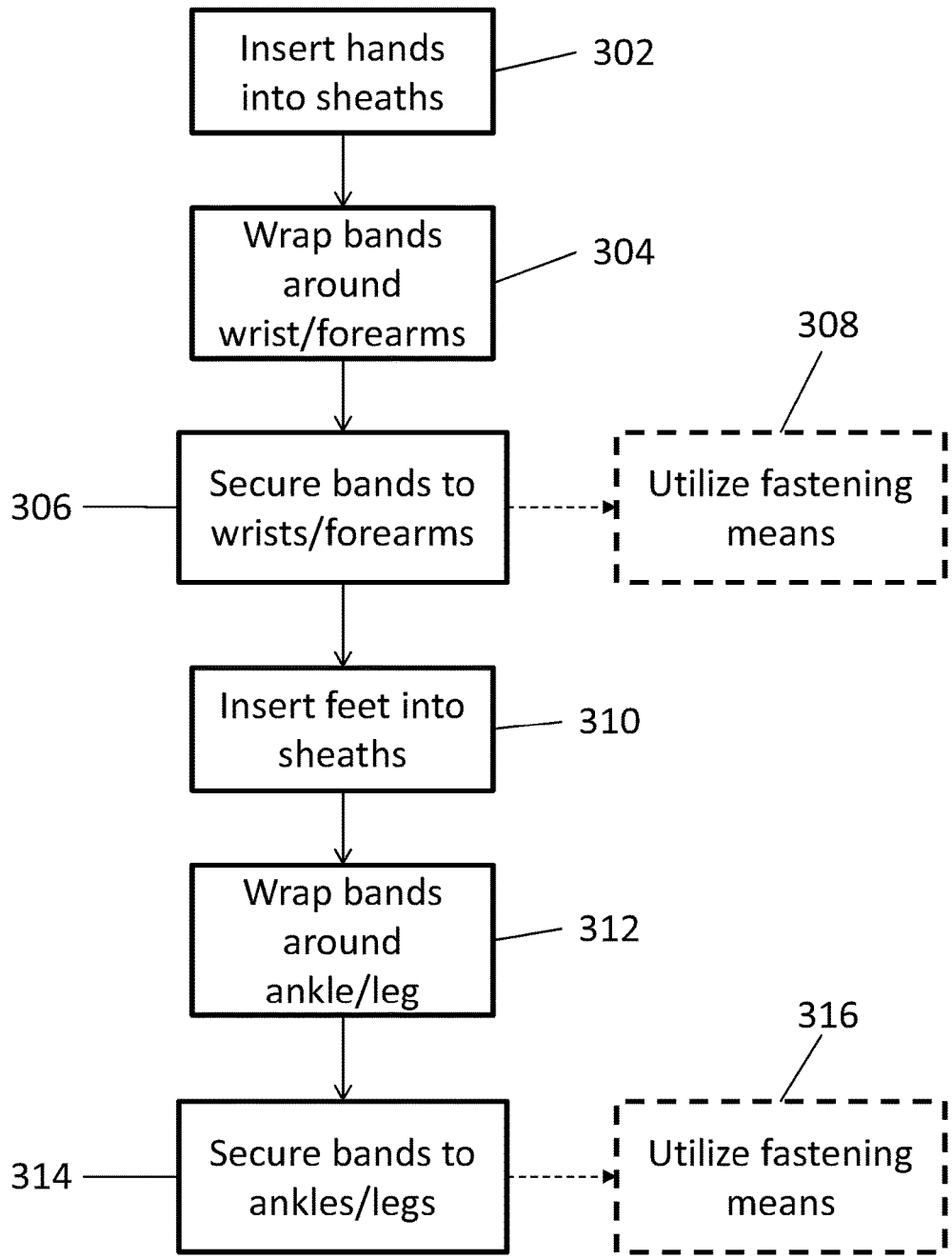
FIG. 6 depicts a flowchart including steps of an exemplary method of using athletic straps.
Figure 7:
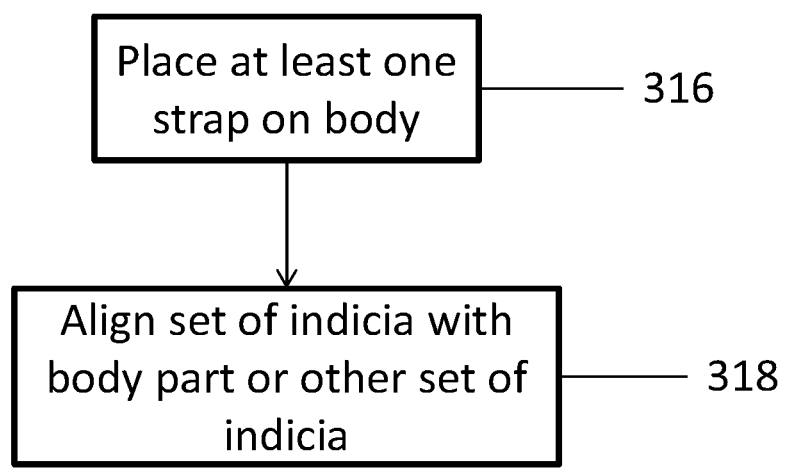
FIG. 7 depicts a flowchart including steps of another exemplary method of using athletic straps.

In the present example, referring to FIG. 6, a user may desire to wear straps (100a, 100b, 200a, 200b) during an exercise, such as a yoga routine, and more particularly, a hot yoga routine. A user may insert each of his hands into the proper sheaths (102) (block 302) and wrap bands (104a, 104b) around the wrists and forearms, such as in one of the manners shown and described herein (block 304). The user may then secure the bands (104a, 104b) to the wrists and forearms in any manner described herein (block 306) such as via fasteners (105) (block 308). A user may also (in no particular order) insert each of his feet into the proper sheaths (202) (block 310) and wrap bands (204a, 204b) around the ankles and legs, such as in one of the manners shown and described herein (block 312). The user may then secure bands (204a, 204b) to the ankles and legs in any manner described herein (block 314), such as via fasteners (205) (block 314).

FIG. 5 shows a perspective view of a user wearing the straps (100a, 100b, 200a, 200b) on the respective hands and feet and the user assuming one exemplary position utilized in an aspect of a yoga practice, for example. As shown, second axes (142, 242) of each sheath (100a, 100b, 200a, 200b) are aligned with one another such that the second sets of indicia (138, 238) extend along a common axis. In addition or in the alternative, straps may be configured such that first and second sets of indicia (136, 138, 236, 238) are oriented at a predetermined angle relative to a particular anatomical structure when worn by a user. For example, first and/or second axes (140, 142, 240, 242) may be oriented at a predetermined angle(s) relative to one or more bones of the foot, ankle, or leg (e.g., tibia, fibula, metatarsals, phalanges, distal phalanges, etc), tendons, ligaments, and other relative anatomical structures. It will be understood that such angles may vary depending on the anatomy of a particular user. It will be further understood that such angles may vary depending on the positioning of the foot, that is, whether the foot is in undergoing pronation, supination, dorsiflexion, plantar flexion, inversion, eversion, other movements/positioning, or anatomically possible combinations thereof, or is in a normal resting state. Moreover, such angles, as well as angles $\theta_1$, $\theta_2$, and $\theta_3$ may be configured for a particular type of yoga practices, poses, skill levels of users, etc. In some examples one or both of the first and second sets of indicia may be used as points of reference for positioning body parts relative to the hands and/or feet. For example, in poses where a user bends the knee (e.g., with the foot planted on the ground), overflexion of the knee may be undesirable. Therefore, in some examples, the first or second sets of indicia may be used as a reference point past which the user should not extend his or her knee (looking down past the knee, towards the foot). In one particular example, the user uses the distal most marking of the first set of indicia as a reference point past which the user does not allow his or her knee to travel during the bending of the knee. In such examples, more particularly, the knee should not flex/bend past a particular predetermined angle. Such angle(s) that may be undesirable will be apparent to persons skilled in the art in view of the teachings herein. Suitable other configurations of foot straps (200), such as configurations aiding in alignment of parts of the body relative to the hands, feet, and/or other parts of the body, will be apparent to persons skilled in the art in view of the teachings herein.

Figure 8:
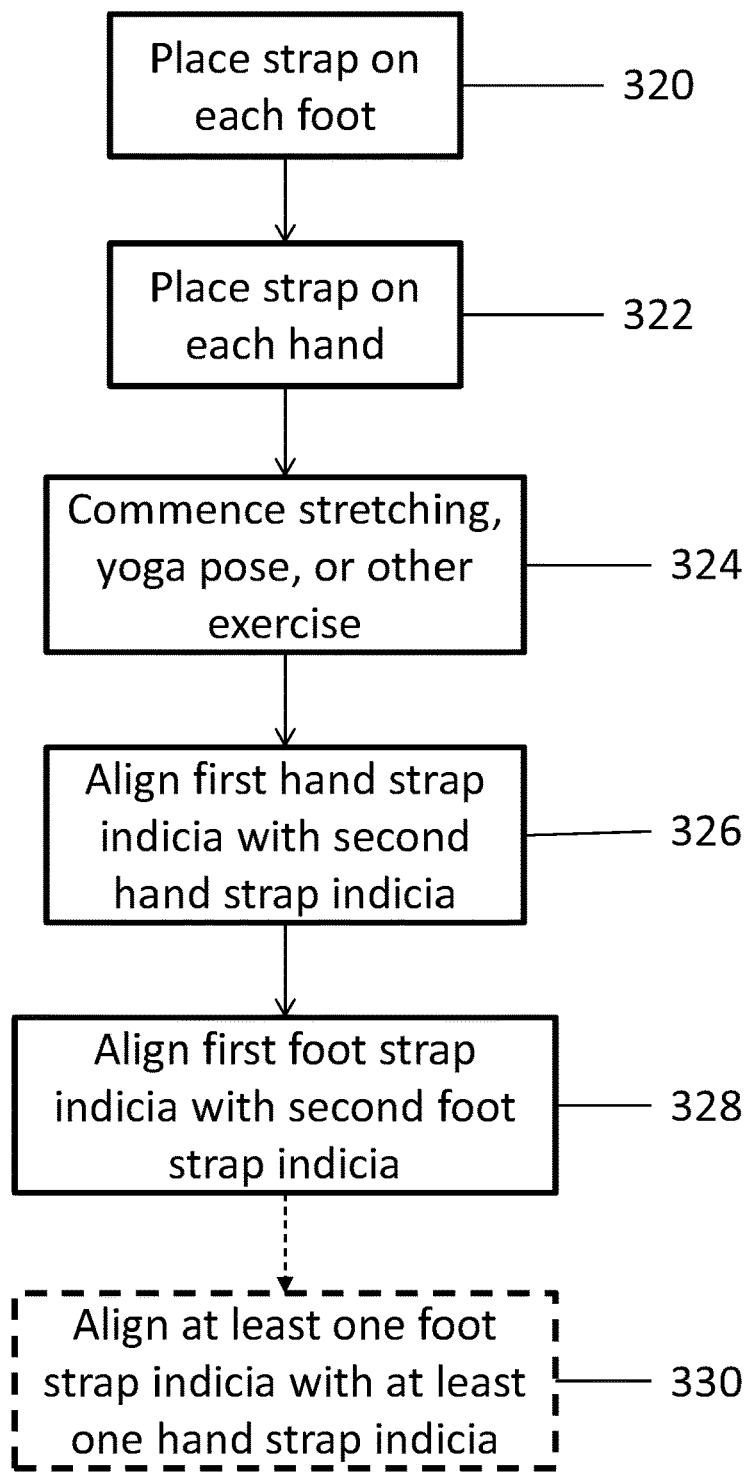
FIG. 8 depicts a flowchart including steps of yet another exemplary method of using athletic straps.

Referring to FIG. 8, a flowchart depicting various exemplary steps of another method of performing an exercise, such as a yoga pose, is shown. For example, a user may desire to perform a "downward facing dog" position. After the user has placed a strap on each foot and on each hand (blocks 320, 322) as described in the present disclosure, the user may commence stretching, a yoga pose, or other exercise (block 324). In the present example, the user may align indicia of a first hand strap (e.g., hand strap (100a)) with indicia of a second hand strap (e.g., hand strap (100b)) (block 326). In the present example, the step in block (326) comprises aligning the first set of indicia (136) of left strap (100a) with the first set of indicia (136) of right strap (136) such that the first axes (140) of each strap (100a, 100b) are coincident. Referring to block (328), a user may also align indicia of a first foot strap (e.g., foot strap (200a)) with indicia of a second foot strap (e.g., foot strap (200b)). In the present example, the step in block (328) comprises aligning the first set of indicia (236) of left strap (200a) with the first set of indicia (236) of right strap (200b) such that the first axes (240) of each strap (200a, 200b) are coincident. Referring to block (330), in some examples, a user may assume a position where he aligns at least one foot strap indicia with at least one hand strap indicia. For example, as shown in FIG. 5, a user may assume a position where the first sets of indicia (136) of each hand strap (100a, 100b) are in alignment with one another and with the first sets of indicia (236) of each foot strap (200a, 200b). However, as will be understood by persons skilled in the art, in other examples and in other yoga positions and poses or other exercises, the alignment described in blocks (326, 328, 330) will vary according to such other positions, poses and exercise.

Figure 9:
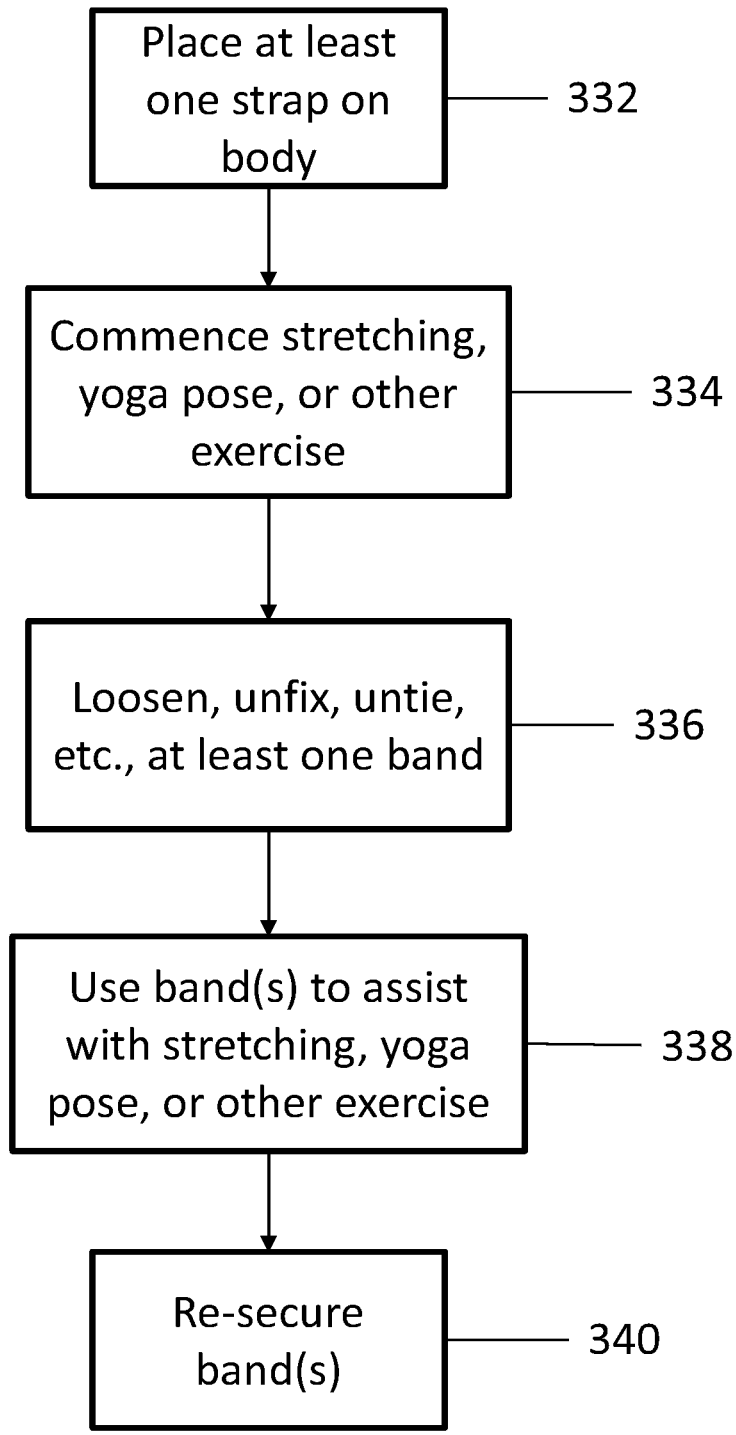
FIG. 9 depicts a flowchart including steps of yet another exemplary method of using athletic straps.
Figure 10:
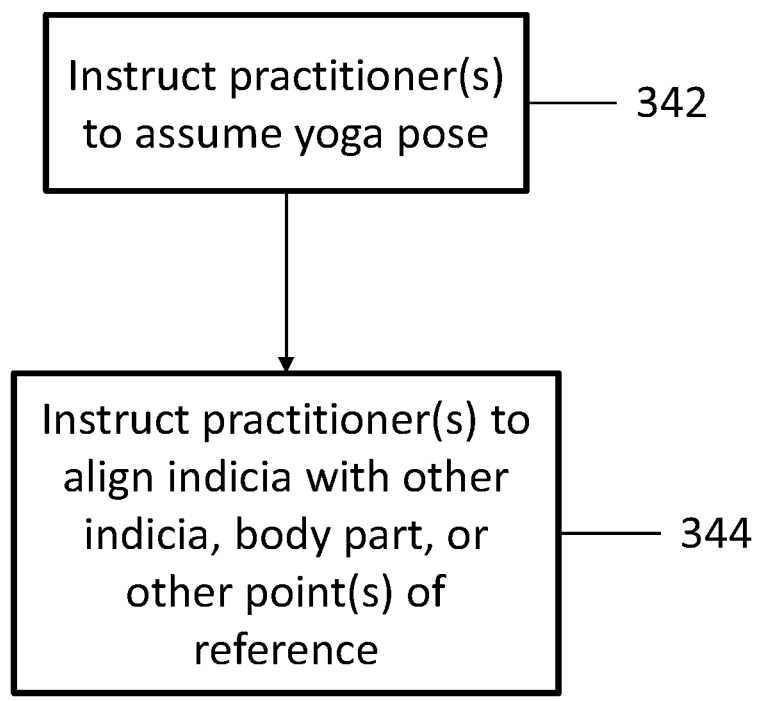
FIG. 10 depicts a flowchart including steps of instructing a yoga exercise.

Referring to FIG. 9, in one embodiment, one or more bands (104a, 104b, 204a, 204b) of the athletic straps (100a, 100b, 200a, 200b) can be used to facilitate to stretching, a yoga pose, or other exercise. Beginners or individuals with injuries may not be able to perform all yoga moves as shown by an instructor, for example. In such situations it may be helpful to use a strap or band, which is often provided by yoga studios, to accommodate certain positions. However, in the middle of a class most students will not walk over to get a band if they do not already have one. The athletic strap, as shown herein, can be quickly untied or unfastened and the strap portion can be used as shown to accommodate a variety of exercise. For example, still referring to FIG. 9, after a user has placed straps (100, 200) on their hands and feet according to the disclosure herein (block 332), respectively, the user may commence stretching, yoga pose, or other exercise (block 334). Upon the desire to perform a yoga move beyond the ability of the user, or for any reason, the user may perform a modified version of the yoga pose, or a simple stretch, or another exercise by loosening or unfixing one or more of bands (104a, 104b, 204a, 204b) (block 336). Alternatively, it will be understood that the user may begin the exercise or practice without having secured one of more of the bands (104a, 104b, 204a, 204b) as described herein. In other examples, bands (104a, 104b, 204a, 204b) may be utilized for assistance while still secured. In the present example, once the band (104a, 104b, 204a, 204b) is free, the user may use one or more of bands (104a, 104b, 204a, 204b) to aid or assist in performing a stretch, yoga pose, or other exercise. Upon completion, the athletic strap can quickly be refastened or secured for normal use (block 340).

Example embodiments of athletic straps that can be worn on the hands or feet are illustrated herein. It will be appreciated that such systems may eliminate the need for a mat, towel, and other equipment that is commonly brought to a yoga session. Such systems may also decrease the need for an instructor as the systems described herein can include reminders on the sheaths or other regions of the athletic straps.

It will be appreciated that any suitable embodiment of an athletic strap is contemplated. For example, pressure sensitive materials can be used that indicate to a user when too much pressure is being placed in an improper area. The sheath or athletic strap can include pressure sensors, or the like, that can be used to record position and placement during a class or session. Such information can be uploaded or otherwise transmitted such that the results can be reviewed and analyzed. Any suitable response or indicator can be associated with pressure sensors, or the like, to help aid with positioning.

Some of the figures can include a flow diagram. Although such figures can include a particular logic flow, it can be appreciated that the logic flow merely provides an exemplary implementation of the general functionality.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

I claim:

1. A method of exercising using an exercise system having (a) a first hand glove portion including: (i) a first plantar aspect, (ii) a first dorsal aspect connected to the first plantar aspect, wherein the first dorsal aspect and the first plantar aspect together define a first cavity, (iii) a first indicium disposed on the first dorsal aspect, wherein the first indicium extends along a first axis; (b) a first foot glove portion comprising: (i) a second plantar aspect, (ii) a second dorsal aspect connected to the second plantar aspect, wherein the second dorsal aspect and the second plantar aspect together define a second cavity, (iii) a second indicium disposed on the second dorsal aspect, wherein the second indicium extends along a second axis, the method comprising:

(a) placing a first hand through the first cavity;
   (b) placing a first foot through the second cavity;
   (c) planting the first foot on a surface; and
   (d) placing the first hand on the surface such that the first indicium is aligned with the second indicium so the first axis and the second axis extend along a common axis.

2. The method of claim 1, wherein the first axis extends laterally relative to the first hand glove portion.

3. The method of claim 2, wherein the second axis extends laterally relative to the first foot glove portion.

4. The method of claim 1, wherein the first axis extends longitudinally relative to the first hand glove portion.

5. The method of claim 4, wherein the second axis extends longitudinally relative to the first foot glove portion.

6. The method of claim 1, further comprising bending a knee associated with the first foot glove portion.

7. The method of claim 6, further comprising bending the knee associated with the first foot such that the knee does not extend distally past the second indicium.

8. The method of claim 6, further comprising being the knee associated with the first foot glove portion while aligning the first indicium with the second indicium.

9. The method of claim 1, wherein the first foot glove portion further comprises a pair of straps extending from either the second plantar aspect or the second dorsal aspect.

10. The method of claim 9, further comprising grasping and pulling the pair of straps.

11. The method of claim 9, wherein the pair of straps are formed from an elastic material.

12. The method of claim 9, wherein the pair of straps further comprising complementary connecting features configured to selectively couple the pair of straps.

13. The method of claim 1, wherein the first hand glove portion comprises a third indicium disposed on the first dorsal portion, wherein the third indicium extends along an third axis perpendicular with the first axis.

14. The method of claim 13, wherein the first foot glove portion comprises a fourth indicium disposed on the second dorsal portion, wherein the fourth indicium extends along a fourth axis perpendicular with the second axis.

15. A method of exercising using an exercise system having (a) a first hand glove portion including: (i) a first plantar aspect, (ii) a first dorsal aspect connected to the first plantar aspect, wherein the first dorsal aspect and the first plantar aspect together define a first cavity, and (iii) a first indicium disposed on the first dorsal aspect, wherein the first indicium extends along a first axis; and (b) a first foot glove portion including: (i) a second plantar aspect, (ii) a second dorsal aspect connected to the second plantar aspect, wherein the second dorsal aspect and the second plantar aspect together define a second cavity, and (iii) a second indicium disposed on the second dorsal aspect, wherein the second indicium extends along a second axis, the method comprising:

(a) placing a first hand through the first cavity;
   (b) placing a first foot through the second cavity;

(c) extending a knee forward associated with the first foot and planting the first foot on a surface;

(d) extending the first hand forward and positioning the first hand on the surface such that the first indicium is aligned with the second indicium so the first axis and the second axis extend along a common axis; and (e) positioning the knee such that the knee does not extend distally past the second indicium.

16. The method of claim 15, wherein the first glove portion further includes a third indicium extending substantially perpendicular with the first indicium, wherein the exercise system further has (a) a second foot glove portion including: (i) a third plantar aspect, (ii) a third dorsal aspect connected to the third plantar aspect, wherein the second dorsal aspect and the second plantar aspect together define a third cavity, and (iii) a fourth indicium disposed on the second dorsal aspect, wherein the second indicium extends along a third axis substantially perpendicular with the second axis, the method further comprising:

(a) inserting a second foot within the third cavity; and (b) aligning the fourth indicium with the third indium of the first hand glove portion while the first indicium and the second indicium are aligned.

17. The method of claim 15, wherein the first axis extends laterally relative to the first hand glove portion.

18. The method of claim 17, wherein the second axis extends laterally relative to the first foot glove portion.

19. The method of claim 15, wherein the first plantar portion and the second plantar portion comprises a tacky material.

20. A method of exercising using an exercise system having (a) a first hand glove portion including: (i) a first plantar aspect comprising a first tacky material, (ii) a first dorsal aspect connected to the first plantar aspect, wherein the first dorsal aspect and the first plantar aspect together define a first cavity, (iii) a first indicium disposed on the first dorsal aspect, wherein the first indicium extends along a first axis; and (b) a first foot glove portion including: (i) a second plantar aspect comprising a second tacky material, (ii) a second dorsal aspect connected to the second plantar aspect, wherein the second dorsal aspect and the second plantar aspect together define a second cavity, and (iii) a second indicium disposed on the second dorsal aspect, wherein the second indicium extends along a second axis, the method comprising:

(a) placing a first hand through the first cavity;

(b) placing a first foot through the second cavity;

(c) planting the first foot on a surface such that the second tacky material engages the surface; and (d) placing the first hand on the surface such that first tack material engages the surface and also such that the first indicium is aligned with the second indicium so the first axis and the second axis extend along a common axis.

* * * * *